(12) United States Patent
Dobbs (10) Patent No.: US 9,368,272 B2
(45) Date of Patent: Jun. 14, 2016

(54) SHIELDED POWER COUPLING DEVICE

(71) Applicant: Analogic Corporation, Peabody, MA (US)

(72) Inventor: John Dobbs, Beverly, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 7 days.

(21) Appl. No.: 14/094,004

(22) Filed: Dec. 2, 2013

(65) Prior Publication Data

US 2014/0085042 A1 Mar. 27, 2014

Related U.S. Application Data

(63) Continuation of application No. PCT/US2011/038777, filed on Jun. 1, 2011, and a continuation-in-part of application No. 13/719,935, filed on Dec. 19, 2012, which is a continuation of (Continued)

(51) Int. Cl.
*H01F 21/06* (2006.01)
*H01F 27/02* (2006.01)
(Continued)

(52) U.S. Cl.
CPC .............. *H01F 27/365* (2013.01); *A61B 6/032* (2013.01); *A61B 6/56* (2013.01); *H01F 27/367* (2013.01); *H01F 38/18* (2013.01); *H01F 41/00* (2013.01); *Y10T 29/4902* (2015.01)

(58) Field of Classification Search
CPC ..... H01F 27/027; H01F 27/292; H01F 38/18; H01F 21/04; H01F 21/06; H01F 29/10; H01F 27/362

USPC ............. 336/65, 83, 115, 120–121, 130–136, 336/84 R, 84 C
See application file for complete search history.

(56) References Cited

U.S. PATENT DOCUMENTS

| | | | |
|---|---|---|---|
| 3,336,662 A | 8/1967 | Howland et al. | |
| 3,999,093 A | 12/1976 | Kirtley, Jr. | |

(Continued)

FOREIGN PATENT DOCUMENTS

| | | | |
|---|---|---|---|
| CA | 20022434479 A1 | 10/2002 | |
| CN | 101026033 A | 8/2007 | |

(Continued)

OTHER PUBLICATIONS

International Search Report and Written Opinion for corresponding PCT Application No. PCT /US08/52326.

(Continued)

*Primary Examiner* — Tsz Chan
(74) *Attorney, Agent, or Firm* — Cooper Legal Group, LLC (57) ABSTRACT

One or more techniques and/or systems described herein provide a shielded power coupling device, such as may be used to transfer electric power from a stator portion of a computed tomography (CT) apparatus to a rotor portion. The shielded power coupling device comprises a rotor portion and a stator portion, separated by an airgap, respectively comprising one or more windings and a core. The shielded power coupling device further comprises a fringe field mitigation element(s) (e.g., an electrically conductive wire) that is configured to carry an induced current that creates a magnetic field that mitigates, or substantially cancels, magnetic flux generated by current in the windings that escapes from the core near the core airgap.

20 Claims, 7 Drawing Sheets

Related U.S. Application Data application No. 11/699,529, filed on Jan. 29, 2007, now Pat. No. 8,350,655, which is a continuation-in-part of application No. 10/787,270, filed on Feb. 26, 2004, now Pat. No. 7,868,723.

(60) Provisional application No. 60/450,038, filed on Feb. 26, 2003.

(51) Int. Cl.
| | |
|---|---|
| H01F 27/36 | (2006.01) |
| H01F 21/04 | (2006.01) |
| H01F 41/00 | (2006.01) |
| A61B 6/03 | (2006.01) |
| A61B 6/00 | (2006.01) |
| H01F 38/18 | (2006.01) |

(56) References Cited

U.S. PATENT DOCUMENTS

| | | |
|---|---|---|
| 4,145,591 A | 3/1979 | Takeda |
| 4,156,192 A | 5/1979 | Schedrovitsky et al. |
| 4,259,654 A | 3/1981 | Persson et al. |
| 4,293,884 A | 10/1981 | Schiller |
| 4,323,781 A | 4/1982 | Baumann et al. |
| 4,335,423 A | 6/1982 | Koizumi et al. |
| 4,496,202 A | 1/1985 | Beckmann et al. |
| 4,564,812 A | 1/1986 | Van Dijk |
| 4,628,426 A | 12/1986 | Steigerwald |
| 4,725,781 A | 2/1988 | Roschmann |
| 4,785,246 A | 11/1988 | Sugimoto |
| 4,798,540 A | 1/1989 | Bernardi |
| 4,912,735 A | 3/1990 | Beer |
| 5,023,768 A | 6/1991 | Collier |
| 5,105,095 A | 4/1992 | Rudy et al. |
| 5,191,309 A | 3/1993 | Laros |
| 5,296,810 A | 3/1994 | Morich |
| 5,347,256 A | 9/1994 | Yumiki et al. |
| 5,414,360 A | 5/1995 | Westphal et al. |
| 5,499,281 A | 3/1996 | Weedon et al. |
| 5,512,828 A | 4/1996 | Pausch et al. |
| 5,530,425 A | 6/1996 | Harrison |
| 5,570,073 A | 10/1996 | Muller |
| 5,572,129 A | 11/1996 | Carlson |
| 5,572,178 A | 11/1996 | Becker et al. |
| 5,608,771 A | 3/1997 | Steigerwald et al. |
| 5,717,552 A | 2/1998 | Varian |
| 5,827,445 A | 10/1998 | Yoshida et al. |
| 5,841,067 A | 11/1998 | Nakamura et al. |
| 5,939,882 A | 8/1999 | Gebhardt et al. |
| 5,986,531 A | 11/1999 | Carrozzi |
| 6,015,476 A | 1/2000 | Schlueter et al. |
| 6,058,000 A | 5/2000 | Koenck et al. |
| 6,160,869 A | 12/2000 | Zapalac et al. |
| 6,236,209 B1 | 5/2001 | Arz et al. |
| 6,239,361 B1 | 5/2001 | Snaper |
| 6,256,175 B1 | 7/2001 | Zhang |
| 6,326,788 B1 | 12/2001 | Mulder et al. |
| 6,346,816 B1 | 2/2002 | Damadian et al. |
| 6,351,123 B1 | 2/2002 | Gebhardt |
| 6,351,626 B1 | 2/2002 | Lohr |
| 6,373,921 B1 | 4/2002 | Kliman et al. |
| 6,388,548 B1 * | 5/2002 | Saito et al. ............... 336/90 |
| 6,407,470 B1 | 6/2002 | Seelig |
| 6,437,571 B1 | 8/2002 | Danby et al. |
| 6,448,500 B1 | 9/2002 | Hosaka et al. |
| 6,469,508 B1 | 10/2002 | Damadian et al. |
| 6,496,007 B1 | 12/2002 | Damadian et al. |
| 6,501,016 B1 | 12/2002 | Sosnowski |
| 6,576,877 B2 | 6/2003 | Dabelstein et al. |
| 6,590,305 B2 | 7/2003 | Wang et al. |
| 6,590,391 B1 | 7/2003 | Shudo et al. |
| 6,590,953 B2 | 7/2003 | Suzuki et al. |
| 6,617,852 B1 | 9/2003 | Danby et al. |
| 6,636,406 B1 | 10/2003 | Anthony |
| 6,653,924 B2 | 11/2003 | Vinciarelli et al. |
| 6,687,108 B1 | 2/2004 | Anthony et al. |
| 6,713,737 B1 | 3/2004 | Verhagen |
| 6,762,088 B2 | 7/2004 | Acosta et al. |
| 6,794,792 B2 | 9/2004 | Wang |
| 6,839,401 B2 | 1/2005 | Nokita |
| 7,425,096 B2 | 9/2008 | Beyerlein et al. |
| 7,717,619 B2 | 5/2010 | Katcha et al. |
| 2004/0000974 A1 | 1/2004 | Odenaal et al. |
| 2005/0030013 A1 | 2/2005 | Terada et al. |
| 2005/0090732 A1* | 4/2005 | Ivkov et al. ............... 600/411 |
| 2005/0140483 A1 | 6/2005 | Wobben |
| 2006/0022785 A1 | 2/2006 | Dobbs |
| 2006/0208727 A1 | 9/2006 | Matsumoto et al. |
| 2007/0188284 A1 | 8/2007 | Dobbs |
| 2008/0049904 A1 | 2/2008 | Beyerlein et al. |
| 2008/0067873 A1 | 3/2008 | Zhou et al. |
| 2009/0304144 A1 | 12/2009 | Beyerlein et al. |

FOREIGN PATENT DOCUMENTS

| | | |
|---|---|---|
| CN | 101632141 | 1/2010 |
| DE | 102004035603 A1 | 3/2006 |
| DE | 102004051170 A1 * | 5/2006 |
| EP | 0926690 A1 | 6/1999 |
| GB | 0990418 | 4/1965 |
| GB | 1321940 A | 7/1973 |
| JP | 61020308 A | 1/1986 |
| JP | 61140116 A * | 6/1986 |
| JP | 63192212 A | 8/1988 |
| JP | 01123406 | 5/1989 |
| JP | 2211123 A1 | 8/1990 |
| JP | 06181124 | 6/1994 |
| JP | 08051039 | 2/1996 |
| JP | 8335511 A1 | 12/1996 |
| JP | 11354346 | 12/1999 |
| JP | 2000114077 A * | 4/2000 |
| JP | 2001015363 A | 1/2001 |
| JP | 2001338820 A | 12/2001 |
| JP | 2000114077 | 7/2002 |
| JP | 2002198238 | 7/2002 |
| JP | 2003114203 A | 4/2003 |
| JP | 2003114203 A1 | 4/2003 |
| JP | 2004166923 A | 6/2004 |
| JP | 2010517309 A | 5/2010 |
| WO | WO2006008274 | 1/2006 |
| WO | 2010102987 A1 | 9/2010 |
| WO | WO 2012035100 A1 * | 3/2012 |

OTHER PUBLICATIONS

Crepaz et al. The Reduction of the External Electromagnetic Field Produced by Reactors and Inductors for Power Electronics, ICEM, 1986, pp. 419-423.

Miyoshi et al. Reduction of Magnetic Flux Leakage From an Induction Heating Range, IEEE Transactions on Industry Applications, vol. 1A-19, No. 4, Jul./Aug. 1983.

Pedder et al. A Contactless Electrical Energy Transmission System, IEEE Transactions on Industrial Electronics, vol. 46, No. 1, Feb. 1999.

Williamson Labs, http://www.williamson-labs.com/480_shi.htm.

Supplementary European Search Report dated Jan. 3, 2011 from corresponding European Application No. 08728478.2.

International Search Report and Written Opinion for corresponding application: PCT/US11/038777, dated Oct. 19, 2011, 21 pages.

European Office action for corresponding application: 11725574.5, dated Sep. 25, 2014, 5 pages.

Response to European Office action dated Jan. 19, 2015, 10 pages.

Restriction/Election Office Action cited in U.S. Appl. No. 13/706,822 dated Mar. 20, 2014, 10 pgs.

Preliminary Amendment cited in U.S. Appl. No. 13/719,935 dated Mar. 15, 2013, 7 pgs.

Restriction/Election Office Action cited in U.S. Appl. No. 13/719,935 dated May 12, 2014, 7 pgs.

Reply Restriction/Election Office Action cited in U.S. Appl. No. 13/719,935 dated Jul. 14, 2014, 3 pgs.

(56) References Cited

OTHER PUBLICATIONS

Non-Final Office Action cited in U.S. Appl. No. 13/719,935 dated Sep. 18, 2014, 60 pgs.
Reply Non-Final Office Action cited in U.S. Appl. No. 13/719,935 dated Dec. 18, 2014, 18 pgs.
Int. Preliminary Report cited in PCT Application No. PCT/US2011/038777 dated Dec. 2, 2013, 16 pgs.
Korean Office Action cited in Japanese Application No. 2014-513485 dated Mar. 10, 2015, 3 pgs.
Final Office Action cited in U.S. Appl. No. 13/719,935 dated Jun. 30, 2015, 63 pgs.
Reply Final Office Action cited in U.S. Appl. No. 13/719,935 dated Sep. 30, 2015, 20 pgs.
Chinese Office Action cited in Chinese Application No. 201180071384.0 dated Oct. 20, 2015, 8 pgs.

\* cited by examiner

SHIELDED POWER COUPLING DEVICE

RELATED APPLICATION

This application claims priority to International Application PCT/US2011/038777, filed Jun. 1, 2011 and entitled "SHIELDED POWER COUPLING DEVICE." This application also claims priority to U.S. patent application Ser. No. 13/719,935, filed Dec. 19, 2012 and entitled "SHIELDED POWER COUPLING DEVICE," which is a continuation of U.S. patent application Ser. No. 11/699,529, filed on Jan. 29, 2007 and entitled "SHIELDED POWER COUPLING DEVICE," which is a continuation-in-part of U.S. patent application Ser. No. 10/787,270, filed on Feb. 26, 2004 and entitled "POWER COUPLING DEVICE," which claims priority to U.S. Provisional Application No. 60/450,038, filed on Feb. 26, 2003 and entitled "Non-Contacting Power Coupling Device". Applications PCT/US2011/038777, Ser. Nos. 13/719,935, 11/699,529, 10/787,270, and 60/450,038 are incorporated herein by reference.

BACKGROUND

The present application relates to a shielded power coupling device configured to transfer electric power between a rotating object (e.g., a rotor) and a stationary object (e.g., a stator) and/or between two rotating objects. It finds particular application in the context of computed tomography (CT) scanners, such as might be used in medical, security, and/or industrial applications. For example, the shielded power coupling device may be configured to transfer electric power from a stationary portion to a rotating gantry that houses a radiation source and a detector array. It also relates to other applications where a power coupling device that reduces RF emissions and/or other electromagnetic interferences, reduces leakage inductance, and/or improves efficiency during inductive transfer of electric power may be useful.

Systems that comprise electronic components within a rotating unit often require power to be provided to the rotating unit via a power coupling apparatus. For example, in CT scanners, power is supplied to electronics on a rotating gantry of the CT scanner using a power coupling device. Traditionally, these power coupling devices have been slip-ring/brush assemblies. Slip-rings transfer electricity between a stationary member and a rotating member (e.g., or between two rotating members), through the contact of two materials (e.g., via a sliding contact). Slip-ring assemblies typically comprise two or more continuous conducting rings and one or more brushes on respective rings for delivering current to and from the rings.

Ordinarily, numerous slip-rings are used in order to supply different voltage levels to electronic components of the rotating unit (e.g., as required by the various electronic components of the rotating units). While the use of brushes and slip-rings has proven effective for supplying power to electronics comprised in a rotating unit, conventional brush and slip-ring mechanisms tend to be dirty, unreliable, and/or noisy. For example, the brushes can break down to create metallic dust overtime, which may cause problems with ultra-sensitive electronics. Moreover, in some applications, such as where sensitive diagnostic/imaging procedures are being performed (e.g., such as in CT imaging), the electric noise inherent in the power being transferred and/or generated by the brushes can cause interference with the procedures. Other drawbacks of slip-ring assemblies include the cost and complexity of manufacture due to the special materials and/or the mechanical precision that is generally required.

Numerous solutions have been proposed to transfer power to electronic components of a rotating gantry without using slip-rings. For example, U.S. Pat. No. 4,323,781 to Baumann discloses an inductive transformer for transmitting energy to an x-ray tube in a rotatable CT-scanning system. The inductive transformer in the Baumann patent consists of primary and secondary windings. An alternating current passing through the primary winding induces a current in the secondary winding. The primary winding is stationary with respect to the scanning system, whereas the secondary winding rotates with the scanning system and provides power to the rotating x-ray tube.

U.S. Pat. No. 4,912,735 to Beer discloses a similar concept, namely a power transfer apparatus including two concentric rings mounted on a static member and a rotating member, respectively. The rings have opposed annular faces, respectively containing a groove. Conductive windings in respective grooves provide an inductive coupling means for coupling power to the rotating gantry in the CT scanner. U.S. Pat. No. 5,608,771 to Steigerwald applies a substantially similar concept to a quasi-resonant high voltage generation scheme.

Although the devices discussed above allow for power transfer to rotating systems without the need for slip-rings, they suffer from a number of drawbacks. For example, these devices do not provide to the user the flexibility of transferring power between a plurality of input and output voltages as is useful in some applications, such as in CT scanners. Further, these solutions provide few options to the user for adjusting the current and voltage in the power transfer device so as to achieve a desired (e.g., optimal) power transfer efficiency. Moreover, it will be appreciated that these solutions do not consider shielding. The lack of adequate shielding may, for example, result in undesirable RF emission, which may be particularly undesirable in applications that are sensitive to such results, such as CT scanners, for example.

SUMMARY

Aspects of the present application address the above matters, and others. According to one aspect, a shielded power coupling device configured to transfer electric power between a stator and a rotor is provided. The device comprises an inductive field generating element configured to convert electric power to an inductive coupling field. The device also comprises an inductive field receiving element configured to convert the inductive coupling field to electric power. The device further comprises a primary and secondary core separated by a core airgap. The device also comprises a shell, the shell comprising a fringe field mitigation element and a non-fringe field mitigation element. The fringe field mitigation element comprises an electrically conductive material and is configured to mitigate magnetic flux generated by at least one of the inductive field generating element and the inductive field receiving element that escapes from at least one of the primary core and the secondary core near the core airgap.

According to another aspect, a method of constructing a shielded power coupling device configured to transfer electric power between a stator and a rotor is provided. The method comprises constructing a shell of the power coupling device, the shell comprising at least one of a dielectric material, segments of dielectric material, and segments of electrically conductive material. The method also comprises inserting into a portion of the shell a fringe field mitigation element configured to mitigate magnetic flux.

According to yet another aspect, a shielded power coupling device for use in a computed tomography apparatus is provided. The device comprises an inductive field generating element configured to convert electric power to an inductive coupling field and an inductive field receiving element configured to convert the inductive coupling field to electric power. The device also comprises a primary and secondary core separated by a core airgap. The device further comprises a shell comprising at least two segments that are fastened together to form a substantially toroidal structure, the shell comprising a fringe field mitigation element that is configured to mitigate magnetic flux, escaping from at least one of the primary core and the secondary core near the core airgap, that is generated by at least one of the inductive field generating element and the inductive field receiving element.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a shielded power coupling device, or more particularly, to a shielded power coupling device capable of reducing RF emission and/or other electromagnetic interference, reducing leakage inductance, and/or improving efficiency during inductive transfer of electric power in the context, for example, of a computed tomography (CT) scanner such as might be used in medical, security, industrial applications and/or the like and/or in the context of other such applications where transfer of electric power between or among bodies configured to engage in relative rotation is desired.

As used herein, the terms "electromagnetic interference," "radio frequency (RF) emission," and the like can in their most general senses comprise interference from surrounding equipment as it affects operation of a power coupling device(s) in accordance with an embodiment(s) of the present disclosure, but such terms are especially intended to refer to interference generated by the power coupling device(s) in accordance with an embodiment(s) of the present disclosure, particularly as it would affect sensitive electronic equipment such as might comprise a portion(s) of CT scanner(s) or such as might be used in conjunction with a CT scanner(s) or other such systems in the context of which the power coupling device(s) in accordance with embodiments of the present disclosure may be used.

Although the singular may be used herein for convenience in introducing terms such as "body," "object," "stator," "rotor," "airgap," "shield," "core," "winding," "center," "axis," etc., a similar situation will of course exist, and the present disclosure and/or claimed subject matter should be understood to, in general, be applicable where plurality or pluralities of one or more of such features is or are present. Conversely, where plurality or pluralities are discussed, this is not to necessarily exclude the singular. Also, with regard to usage of prepositions "between" and "among," except where otherwise clear from context, use of "between" is not intended to necessarily imply limitation to two objects, and use of "among" is not intended to necessarily imply limitation to more than two objects.

Note that the term "noncontact" is used herein to refer to the ability to transfer power in inductive fashion between or among bodies configured for relative rotation, and should not be understood to necessarily preclude possible contact between or among such bodies for other purposes, including, for example, electrostatic discharge, exchange or transmission of data, mechanical drive or support, braking and safety mechanisms, low-voltage power transfer, and/or high-voltage power transfer, etc. such as might be desired in addition to power transferred inductively by the types of power coupling devices disclosed herein.

It should also be noted that in the present specification, except where otherwise clear from context, the terms "gap" and "airgap" are used more or less interchangeably; although the term "airgap" may be used herein, as this should be understood to be mere deference to convention, it should be understood that such gaps are not limited to air, it being possible for vacuum, oil, and/or other fluid and/or gas, and/or sliding and/or roller bearings or other such contrivances permitting relative movement to completely or partially fill such spaces.

Figure 1:
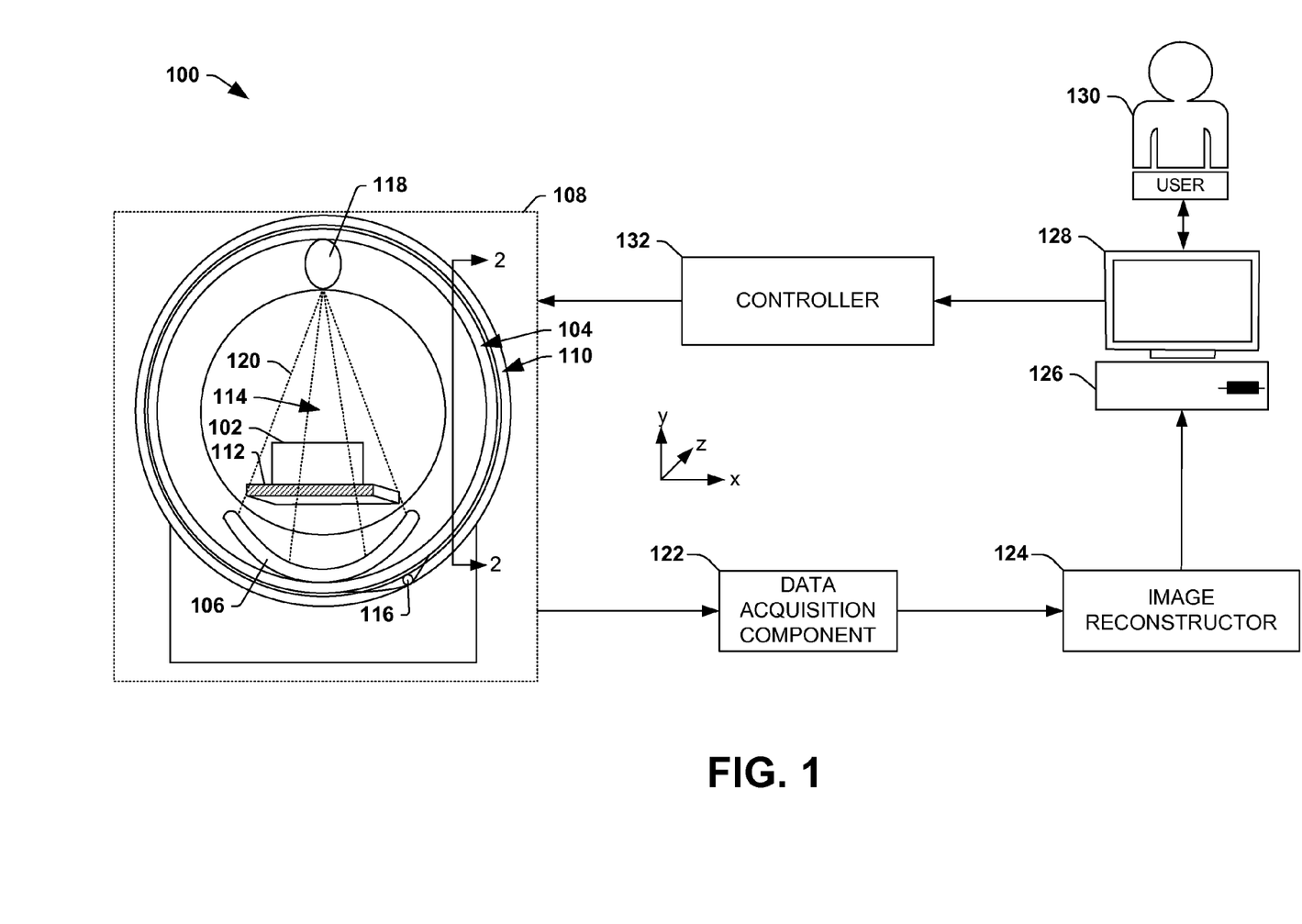
FIG. 1 is a schematic block diagram illustrating an example environment for using a shielded power coupling device such as described herein.

FIG. 1 is an illustration of an example environment 100 in which a shielded power coupling device as described herein may be useful. More particular, FIG. 1 illustrates an example computed tomography (CT) apparatus that can be configured to acquire volumetric information regarding an object 102 under examination and generate two-dimensional and/or three-dimensional images therefrom.

It will be appreciated that while a CT apparatus is described herein, the instant application is not intended to be so limited. That is, to the extent practical, the instant application, including the scope of the claimed subject matter, is intended to be applicable to other apparatuses that comprise a rotor (e.g., a rotating component) and a stator (e.g., a stationary component) and/or two rotating components. More particularly, the instant application is applicable to other apparatuses where supplying electric power to a rotating portion of the apparatus, or to electronic components comprised therein, would be useful. Moreover, the example environment 100 merely illustrates an example schematic and is not intended to be interpreted in a limiting manner, such as necessarily specifying the location, inclusion and/or relative arrangement of the components described herein. For example, a data acquisition component 122 as illustrated in FIG. 1 may be part of a rotor 104 portion of the examination apparatus, or more particularly may be part of a detector array 106, for example.

In the example environment 100, an object examination apparatus 108 configured to examine one or more objects 102 (e.g., a series of suitcases at an airport, a human patient, etc.). The object examination apparatus 108 can comprise a rotor 104 and a stator 110. During an examination of the object(s) 102, the object(s) 102 can be placed on a support article 112, such as a bed or conveyor belt, that is selectively positioned in an examination region 114 (e.g., a hollow bore in the rotor 104), and the rotor 104 can be rotated about the object(s) 102 by a rotator 116 (e.g., motor, drive shaft, chain, etc.).

The rotor 104 may surround a portion of the examination region 114 and may comprise one or more radiation sources 118 (e.g., an ionizing x-ray source) and a detector array 106, which may also be referred to herein as merely a detector, that is mounted on a substantially diametrically opposite side of the rotor 104 relative to the radiation source(s) 118.

During an examination of the object(s) 102, the radiation source(s) 118 emits fan, cone, wedge, and/or other shaped radiation 120 configurations into the examination region 114 of the object examination apparatus 108. It will be appreciated to those skilled in the art that such radiation may be emitted substantially continuously and/or may be emitted intermittently (e.g., a short pulse of radiation is emitted followed by a resting period during which the source is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to compile signals that were transmitted within a predetermined time interval, or measurement interval, using techniques known to those skilled in the art (e.g., binning, integration, etc.). It will be appreciated that such a measurement interval may be referred to by those skilled in the art as a "view" and generally reflects signals generated from radiation 120 that was emitted while the radiation source 118 was at a particular angular range relative to the object 102. Based upon the compiled signals, the data acquisition component 122 can generate projection data indicative of the compiled signals, for example.

The example environment 100 further comprises an image reconstructor 124 configured to receive the projection data that is output by the data acquisition component 122. The image reconstructor 124 is configured to generate image data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive user input from the terminal 126 and generate instructions for the object examination apparatus 108 indicative of operations to be performed. For example, the user 130 may want to reexamine the object(s) 102, and the controller 132 may issue a command instructing the support article 112 to reverse direction (e.g., bringing the object(s) 102 back into an examination region 114 of the object examination apparatus 102).

Figure 2:
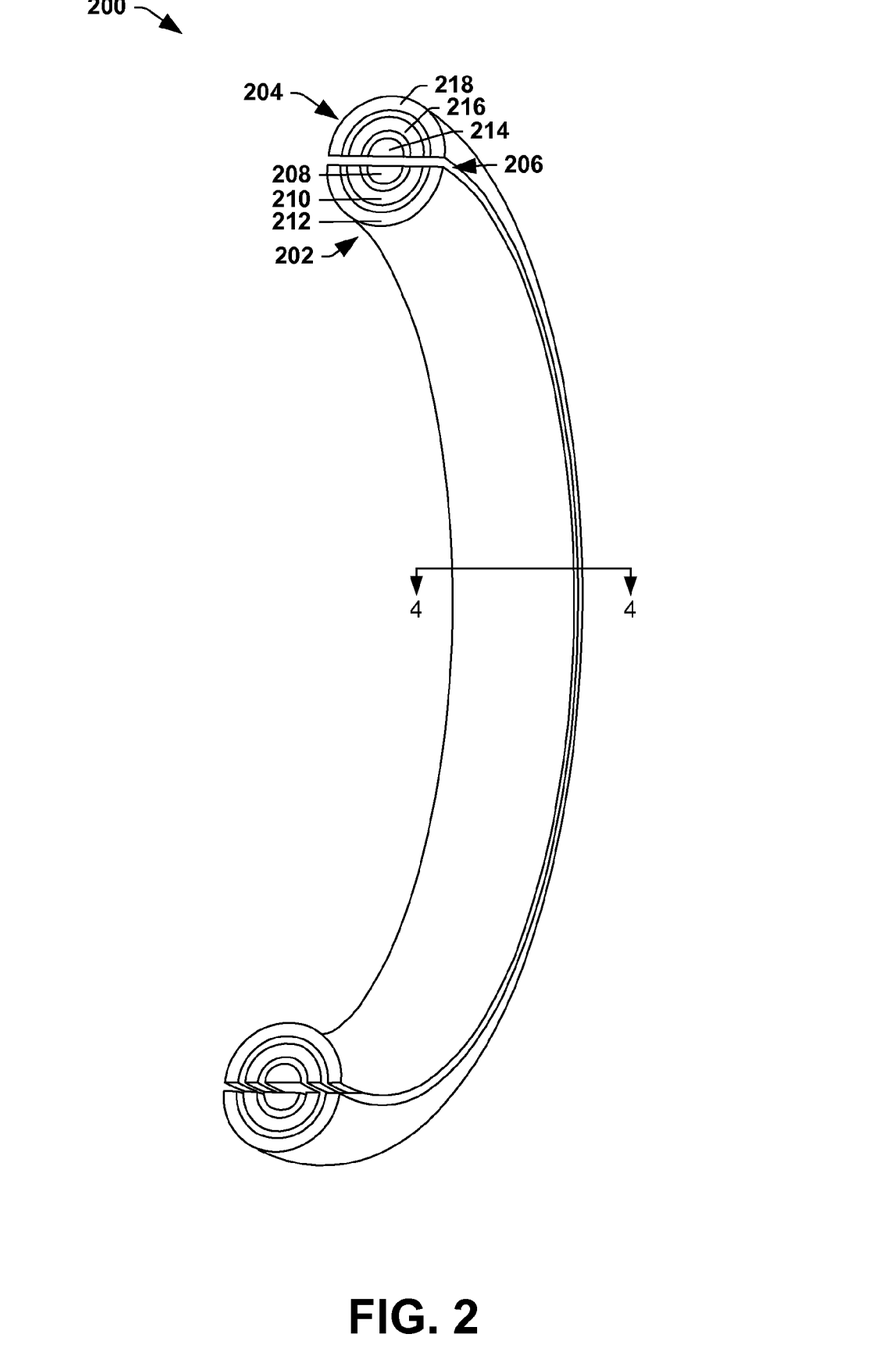
FIG. 2 illustrates an example shielded power coupling device.

FIG. 2 illustrates a cross-sectional view (e.g., taken along line 2-2 in FIG. 1) of an example shielded power coupling device 200 comprising a rotor 202 (e.g., 104 in FIG. 1) and a stator 204 (e.g., 110 in FIG. 1). As illustrated herein, the rotor 202 and the stator 204 are respectively half circles separated from one another via a cylindrical airgap 206, and as will be described below, power is configured to be transferred from the stator 204 to the rotor 202. In this way, power may be supplied to electrical components comprised within the rotor, such as a radiation source (e.g., 118 in FIG. 1) and/or detector array (e.g., 106 in FIG. 1) without using slip-rings and/or brushes, for example.

The rotor 202 and the stator 204 respectively comprise three coaxial half-shells or layers. For example, the rotor 202 comprises, being in order from the airgap 206, a winding 208, a core 210, and a shell 212 (e.g., at least some of which acts as a shield, as described below), and the stator 204 comprises, being in order from the airgap 206, a winding 214, a core 216, and a shell 218 (e.g., which also acts as a shield). It will be appreciated that between the respective layers, there may be gaps of indeterminate thickness (e.g., intended to include the possibility of zero gap).

Note that as used herein, terms such as "half-couple," "half-shell," "half-core," "half-shield," and the like are used as shorthand to refer to one of multiple (e.g., two) parts making up a whole constituting an inductive couple, shell, or the like, and as such should not be interpreted overly literally to mean that there must be exactly two such components or that such components must be of equal size, volume, mass, or the like; nor should a similar implication be drawn from use of the term "couple" (e.g., that there must be exactly two such components). Rather, as used herein, except where otherwise clear from context, such terms should be understood to be representative of the more general case in which multiple parts may make up such a whole. Furthermore, with respect to half-cores and half-shells, for example, the prefix "half-" may sometimes be omitted for convenience of description.

With respect to use of the term "core," this term is used herein to refer generally to reluctance-lowering (alternatively described as magnetically permeable) material, without regard to arrangement of such material in relation to a winding or the like. That is, the term "core" is not to be narrowly interpreted to suggest that such reluctance-lowering material should be axially oriented or centrally located within the turn(s) of a winding as might be the case in a conventional transformer. Instead, the term is used herein out of deference to convention, and may be employed in different embodiments, such as those in which rotary transformers may have so-called reverse topology in which core material is distributed in more or less toroidal fashion to reinforce magnetic flux loops in planes of toroid minor circles around windings wound in the direction of toroid major circles, for example.

Figure 3:
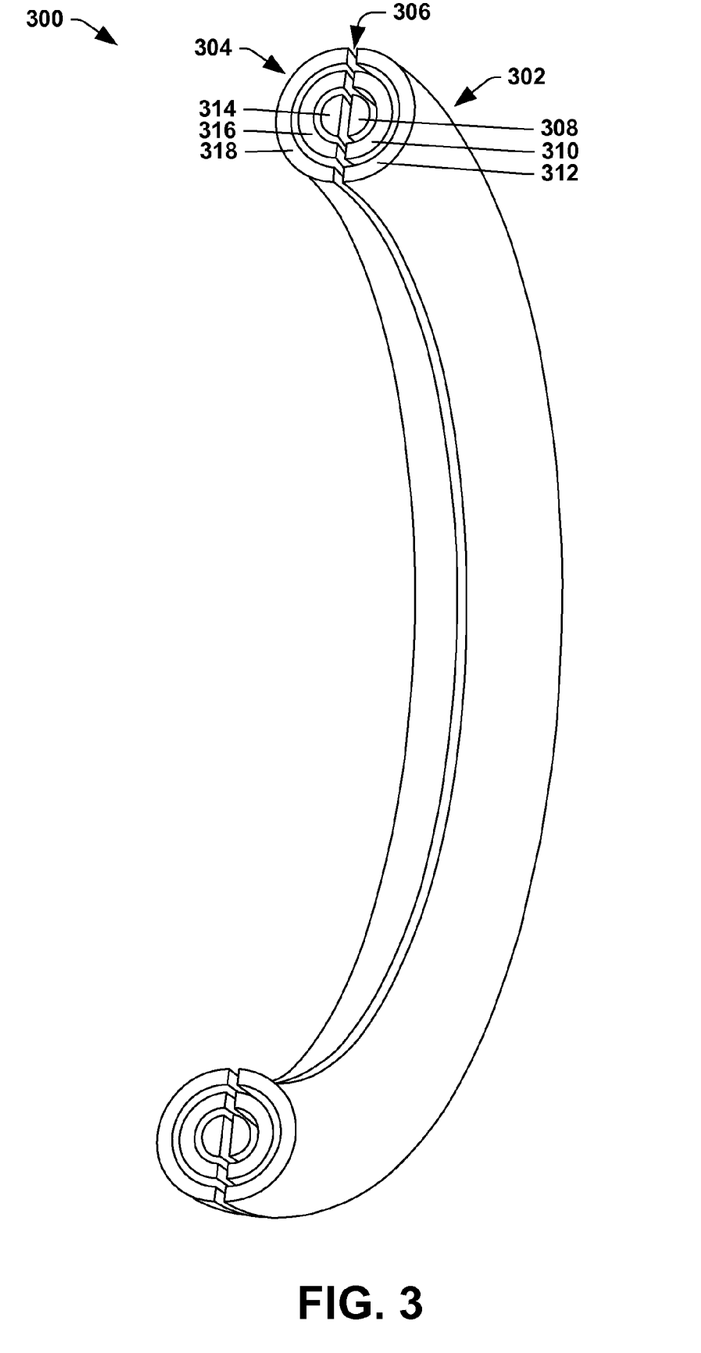
FIG. 3 illustrates an example shielded power coupling device.

FIG. 3 illustrates a cross-sectional view (e.g., taken along line 2-2 in FIG. 1) of an example shielded power coupling device 300 comprising rotor 302 (e.g., 104 in FIG. 1) and stator 304 (e.g., 110 in FIG. 1). As illustrated herein, the rotor 302 and the stator 304 are respectively half circles separated from one another via a planar (e.g., as opposed to a cylindrical) airgap 306, and as will be described below, power is configured to be transferred from the stator 304 to the rotor 302. In this way, power may be supplied to electrical components comprised within the rotor, such as a radiation source (e.g., 118 in FIG. 1) and/or detector array (e.g., 106 in FIG. 1) without using slip-rings and/or brushes, for example.

Similar to that described with respect to FIG. 2, the rotor 302 and the stator 304 respectively comprise three coaxial half-shells or layers. For example, the rotor 302 comprises, being in order from the airgap 306, a winding 308, a core 310, and a shell 312, and the stator 304 comprises, being in order from the airgap 306, a winding 314, a core 316, and a shell 318. It will be appreciated that between the respective layers, there may be gaps of indeterminate thickness (e.g., intended to include the possibility of zero gap).

It will be appreciated that FIGS. 2-3 are merely intended to illustrate example configurations for the rotor 202, 302 and for the stator 204, 304, and that other configurations are contemplated. For example, as will be apparent from FIGS. 4-8, in some embodiments, the rotor 202, 302 and/or the stator 204, 304 may not comprise three coaxial half-shells, and in fact, in some embodiments, at least one of the rotor 202, 302 and/or the stator 204, 304 may comprise substantially zero shielding material depending upon the configurations of the rotor 202, 302 and/or the stator 204, 304. For example, in one embodiment (e.g., such as illustrated in FIG. 7), the shell (e.g., comprising the shielding material) of the rotor 202, 302 may be extended (e.g., to overlap the core 216, 316 and the winding 214, 314 of the stator 204, 304) in such a manner that the stator 204, 304 merely comprises a winding and a core. Moreover, while FIGS. 2-3 illustrate substantially cylindrical and planar airgaps 206, 306, respectively, it will be appreciated that the angle of the airgap may differ from the embodiments herein illustrated. For example, in another embodiment, the airgap could be conical (e.g., where a cylindrical airgap would have a cone angle of substantially zero and a planar airgap would have a cone angle of substantially 180°).

Figure 4:
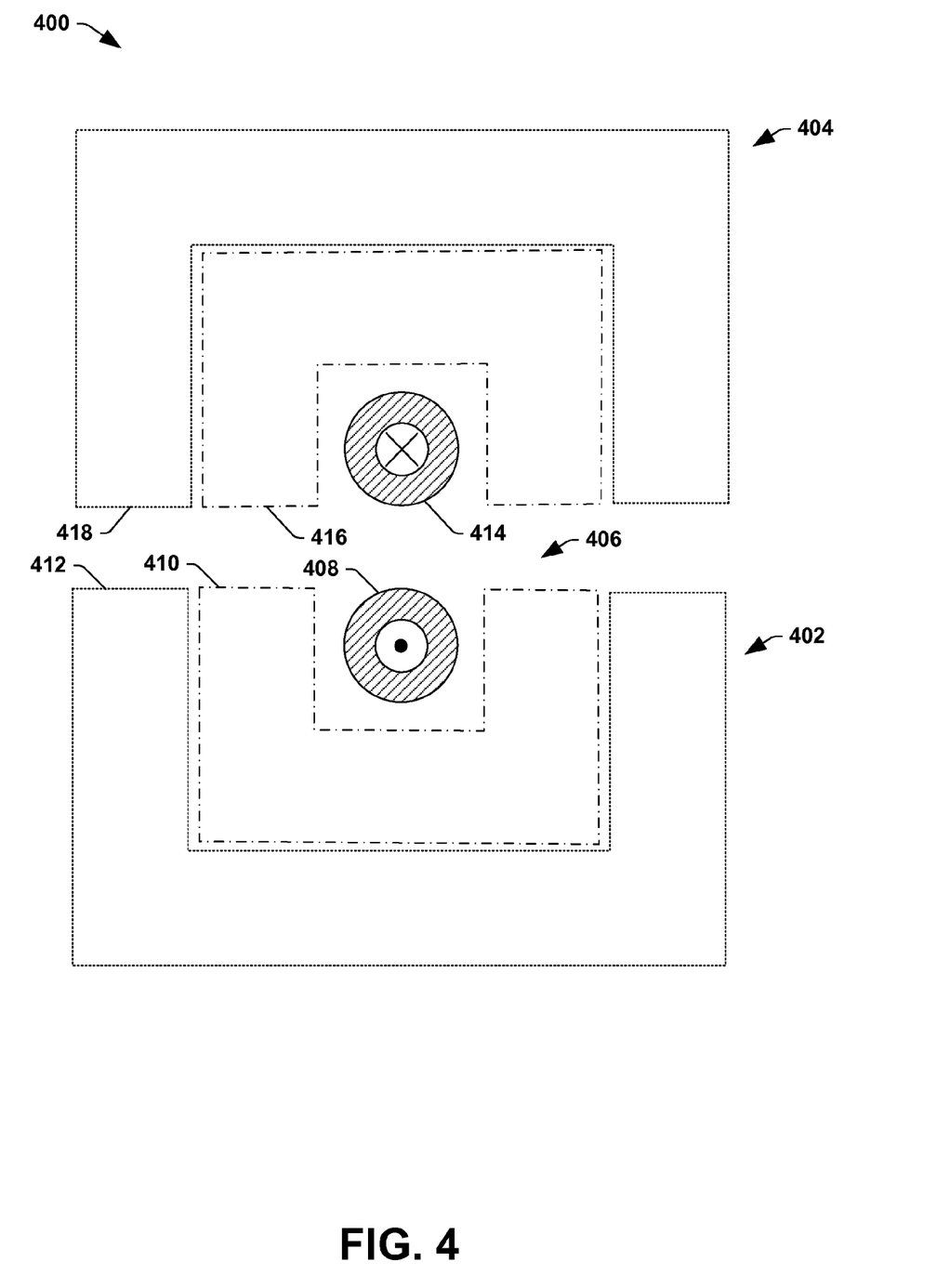
FIG. 4 illustrates a cross-section of a shielded power coupling device.

Referring now to FIG. 4, a cross-sectional view 400 (e.g., taken along line 4-4 in FIG. 2) of a rotor 402 (e.g., 202 in FIG. 2) and a stator 404 (e.g., 204 in FIG. 2) is illustrated. The rotor 402 and the stator 404 respectively comprise three coaxial half-shells or layers. For example, the rotor 402 comprises, being in order from an airgap 406, a winding 408, a secondary core 410, and a shell 412, and the stator 404 comprises, being in order from the airgap 406, a winding 414, a primary core 416, and a shell 418.

The windings 408 and 414 are comprised of more or less circular coils comprising electrically conductive wire (e.g., copper wire) or the like centered on an axis of rotation. It will be appreciated that while FIG. 4 merely illustrates single turn windings, one or both of the windings 404, 414 may instead have multiple turns or fractional turns.

The respective cores 410, 416 generally at least partially surround their respective windings 408, 414 and are configured to increase the coupling between the winding 408 of the rotor 402 and the winding 414 of the stator 404. Generally, the cores 410, 416 are comprised of a ferrite material or other material that is substantially dielectric (e.g., electrically non-conductive), so that electric currents in the cores 410, 416 are mitigated.

In one embodiment, the rotor 402 and the stator 404 are configured like (e.g., perform functions similar to that of) a transformer. For example, in one embodiment, an alternating current (AC) power source may be connected to the winding 414 of the stator 404 (e.g., causing the winding 414 to be an inductive field generating element), and the winding 408 of the rotor 402 may serve as an inductive field receiving element. Moreover, the cores 410, 416 may respectively serve as inductive coupling efficiency increasing elements, for example.

Figure 5:
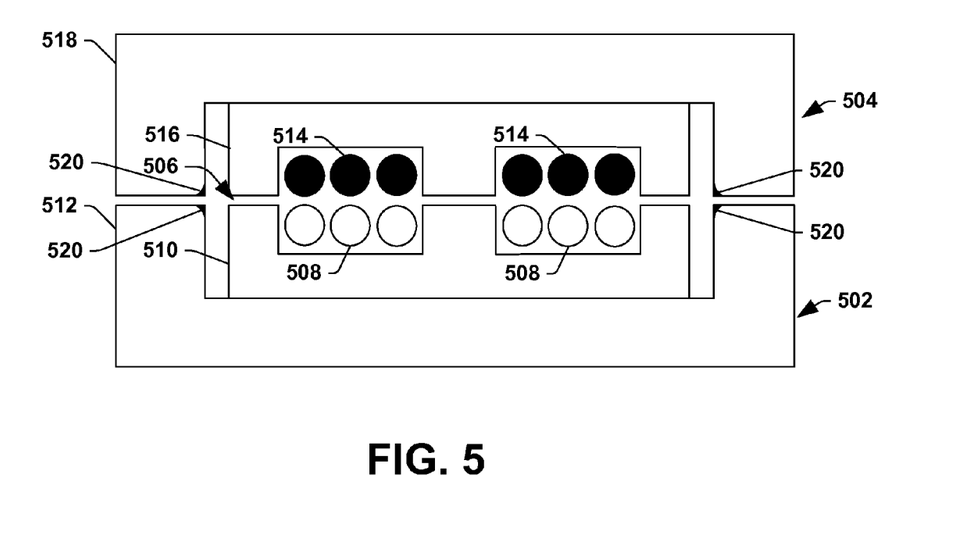
FIG. 5 illustrates a cross-section of a shielded power coupling device illustrating a fringe field mitigation element.
Figure 6:
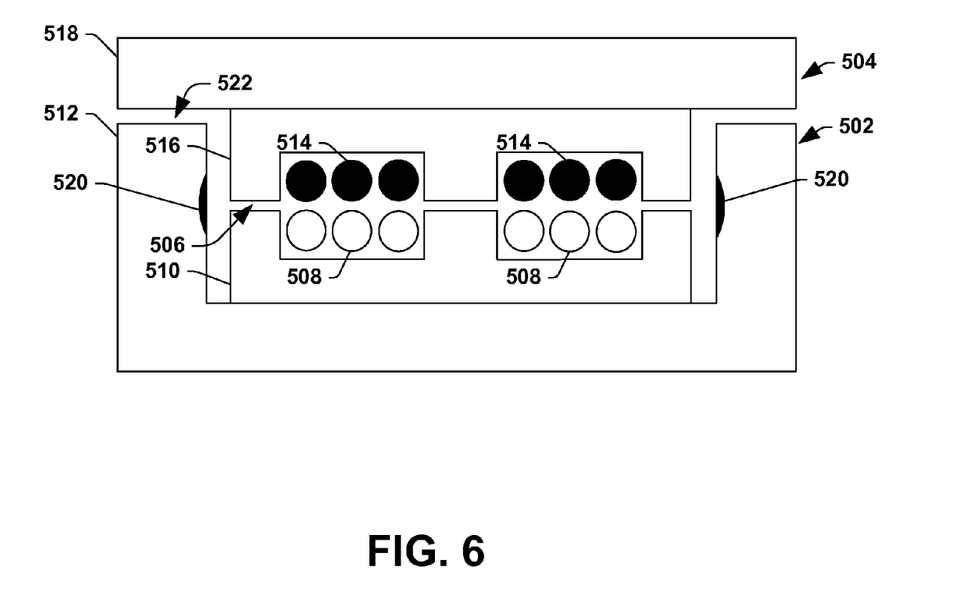
FIG. 6 illustrates a cross-section of a shielded power coupling device illustrating a fringe field mitigation element.
Figure 7:
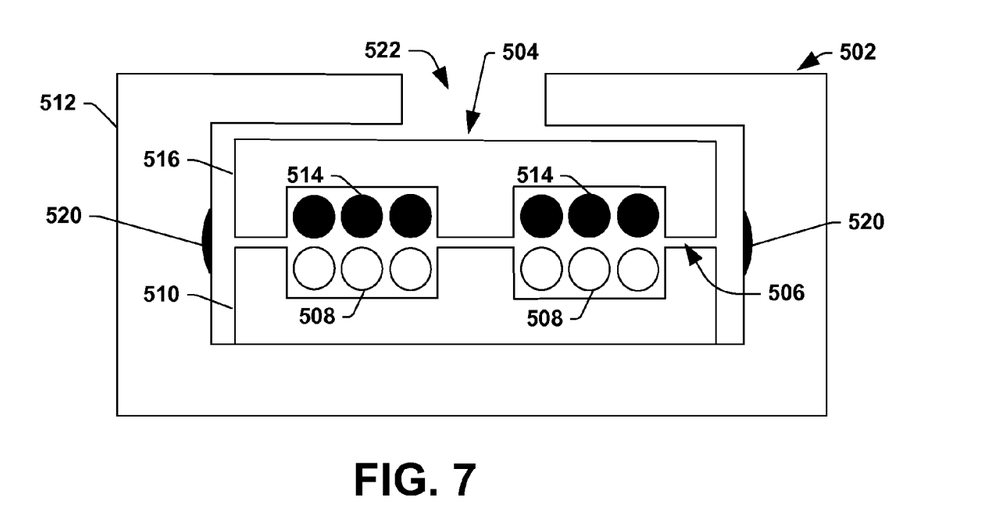
FIG. 7 illustrates a cross-section of a shielded power coupling device illustrating a fringe field mitigation element.

As will be further described with respect to FIGS. 5-7, it will be appreciated that because it is preferred in some applications, such as CT applications, for example, that such power coupling devices be made to operate at frequencies above 20 kHz, it can be expected that the structure of the windings 408, 414 and the cores 410, 416 will generate a dipole field and will radiate strongly to the surrounding space (e.g., creating magnetic field flux loops). The ferrite material or other dielectric material in the respective cores 410, 416 generally channel and/or shunt magnetic field flux loops such that very little magnetic flux would escape therefrom. However, because the core is separated into two separate parts 410, 416 to permit relative rotation, magnetic flux which crosses the core airgap 406 (e.g., an airgap between the two cores 410, 416) may extend beyond the region of the transformer (e.g., escaping through the core near the core airgap 406 and beyond) and induce electric currents at regions of the shell(s) 412, 418 proximate the core airgap 406 if such portions of the shell(s) 412, 418 comprise an electrically conductive material(s) (e.g., such as a copper wire). It will be appreciated that such regions may be referred to herein at fringe field mitigation regions.

Maxwell's equations predict than an oscillating magnetic field (e.g., generated by current flowing in the windings 408, 414) will induce an electric current in the shells 412, 418 that flow in the same direction and are substantially equal in magnitude but opposite in sign to the current in the windings 408, 414. It will be appreciated that the induced currents may be referred to herein as field-cancelling currents and/or image currents because they substantially resemble, except for sign, electric currents flowing in windings 408, 414. Thus, one or both of the shells 412, 418, or rather a fringe field mitigation element(s) of the shells, may be configured to carry a current capable of inducing a magnetic field such as will mitigate (e.g., or cancel) the magnetic field due to the net current in the windings 408, 414. In this way, the shells 412, 418, or rather fringe field mitigation element(s) of the shells 412, 418 (e.g., which will be described in more detail below) act as shields that prevent and/or mitigate the escape of radiation to the exterior of the shells 412, 418 (e.g., where the radiation may cause interference or other deleterious effects with associated, surrounding, etc. electrical components, for example).

As will be described in more detail below, to permit image currents to flow more or less unimpeded (e.g., so that the image currents substantially resemble the currents in the windings 408, 414 and mitigate a magnetic field caused by a net current in the windings 408, 414), it is preferred in one embodiment that the fringe field mitigation element(s) of one or more shells 412, 418 (e.g., approximate the magnetic field generated by current in the windings 408, 414) comprise electrically conductive material forming a substantially continuous electrical path(s) constituting a closed electric circuit(s). In one example, it is furthermore preferred that such a continuous electrical path(s) be capable of supporting an electric current(s) sufficient to induce a magnetic field(s) such as will substantially mitigate or cancel a magnetic field(s) due to electric current(s) flowing in windings 408, 414 during operation of the power coupling device. Such continuous electrical path(s) constituting closed electric circuit(s) around the axis of rotation may, for example, be circular, annular, semitoroidal, and/or may take the form of ring-like band(s) adjacent to and/or alongside core airgap(s). Where such continuous electrical path(s) take the form of ring-like band(s) adjacent to and/or alongside core airgap(s), such ring-like band(s) might be substantially annular for power coupling devices having planar or cylindrical airgaps, and such ring-like band(s) might be substantially conical sections for power coupling devices having conical airgaps, for example.

To better understand the magnetic field(s) generated by the current in the windings 408, 414, that emanate from the airgap 406 for various core/shield geometries and/or to better understand how such magnetic field(s) might be mitigated by a fringe field mitigation element(s) on or near an inner surface(s) of shield(s) 412, 418, reference is now made to FIGS. 5-7.

Referring to FIGS. 5-7, these drawings show results of finite element simulation to determine where current will flow in shield(s) 512, 518 (e.g., 412, 418 in FIG. 4) when the shield(s) 512, 518 is subjected to a magnetic field(s) emanating from a core airgap 506 (e.g., 406) between mutually opposed cores 510, 516 (e.g., 410, 416 in FIG. 4). Although not shown in FIGS. 5-7, an AC power supply is preferably connected to the two three-turn windings 514 disposed on the stator (e.g., the primary windings). It will be appreciated that while FIG. 4 illustrates respective windings 408, 414 as single turn windings, FIG. 5-7 illustrates two multi-turn windings 508 on the rotor 502 and two multi-turn windings 514 on the stator 504. However, for purposes of this disclosure, it is immaterial whether the windings are single-turn or multi-turn windings. That is, the stator 504 (e.g., 404 in FIG. 4) and the rotor 502 (e.g., 402 in FIG. 4) may comprise single-turn windings, multi-turn windings, and/or both, for example.

Where the core material 510, 516 (e.g., a dielectric material, such as ferrite) is discontinuous at the core airgap 506 a magnetic field(s) generated by the current in the windings 508, 514 may leak out of the core material 510, 516 (e.g., and if not contained may interfere with sensitive electronics of an imaging device, for example).

Magnetic fields, or magnetic flux lines, are largely shunted by (e.g., confined within) the core 510, 516, except where magnetic flux crosses the core airgap 506. That is, because the core 510, 516 substantially confines the magnetic flux, leakage generally occurs merely at and/or near the core airgap 506 such that without adequate shielding, a portion of the magnetic flux may escape the core near the core airgap 506 and potentially cause problems with other nearby electronic equipment. However, if there is shielding proximate the core airgap 506 (e.g., a conductive wire as provided herein), the escaping energy may induce a current in the shielding that mitigates potentially deleterious effects caused thereby, for example. Thus, if an induced electric current is generated in portions of the shell(s) 512, 518 approximate the core airgap 506 that is substantially equal in magnitude to electric currents flowing in windings 508, 514 but opposite in sign, the induced electric current may generate a magnetic field that mitigates and/or substantially cancels a magnetic field yielded from the escaping magnetic flux. It will be appreciated that portions of the shell(s) 512, 518 comprising electrically conductive materials for carrying an induced current (e.g., for mitigating the leakage) may be referred to herein as fringe field mitigation elements and for purposes of FIGS. 5-7 are illustrated as darkened portions 520 of the shells 512, 518.

The fringe field mitigations elements 520 of the shield(s) 512, 518 generally comprise an electrically conductive material, such as a small part of the structure which supports the ferrite (if the supporting structure is continuous and conducting) (e.g., a copper and/or an aluminum wire), for example and are configured to carry an induced electric current that is substantially similar (e.g., but opposite in sign) to the current generated by at least one of the inductive field generating element (e.g., the winding 514 of the stator 504) and the inductive field receiving element (e.g., the winding 508 of the rotor 502). In this way, the fringe field mitigation elements 520 are configured to mitigate magnetic flux generated by at least one of the inductive field generating element and the inductive field receiving element (e.g., or their net current), which escapes through the core airgap 506, for example.

Moreover, as discussed above, in one embodiment, it is preferred that the fringe field mitigation elements 520 form substantially continuous electrical paths constituting a closed electric circuit(s) to sustain the induced current for a period of time (e.g., for as long as power is being supplied to the rotor 502 from the stator 504). Stated differently, a discontinuous electric path may cause properties of the induced current, such as its direction, to be altered, causing the magnetic field generated by the induced current to differ from the magnetic field generated by the current in the inductive field generating element and/or in the inductive field receiving element. Thus, whereas a discontinuous electrical path may change properties of the induced current such that the induced current is not sustained, a substantially continuous electrical path may sustain the induced current (e.g., without properties of the current changing over time). For example, in one embodiment, the fringe field mitigation elements 520 may comprise a wire and/or segments of wire that are connected together (e.g., soldered) in such a manner that electric current can flow through the connections substantially unimpeded (e.g., without changing properties of the current).

It will be appreciated that non-fringe field mitigation element(s) of the shells 512, 518 (e.g., portions of the shells 512, 518 that are not darkened), may be comprised of materials that are different than the materials comprised in the fringe field mitigation elements 520. For example, the non-fringe field mitigation elements may comprise a dielectric material (e.g. such as a plastic, paper, pulp, wood, and/or composite material, etc.) and/or a discontinuous electrically conductive material. For example, in one embodiment, the non-fringe field mitigation element(s) of the respective shells 512, 518 are constructed using segments of an aluminum or other metal that are bolted or otherwise fastened together to form the shape of the shells 512, 518 (e.g., to form a substantially toroidal shell). It will be appreciated that because the non-fringe field mitigation element(s) are comprised of segments (e.g., as compared to a continuous metal structure) and are not fastened together (e.g., soldered or welded together) in a manner that forms a substantially continuous electrical path, the non-fringe field mitigation element(s) may not be configured to carry and/or may not be capable of carrying an induced, image current and/or may not be configured to and/or may not be capable of sustaining such an image current as described above.

It will be appreciated that by creating shells 512, 518 that have both a fringe field mitigation element(s) (e.g., a wire) and a non-fringe field mitigation element(s), it might be possible to achieve effective shielding even where the shells 512, 518 have comparatively little electric-current-supporting ability at locations not in the vicinity of the core airgap 506 and/or has discontinuous electrically conductive material at locations not in the vicinity of the core airgap 506. This may, for example, allow a shielded power coupling device to be fabricated that is much less expensive and/or lightweight as compared to conventional devices. For example, inexpensive plastic molded portions may merely be "snapped" or otherwise fastened together with a conductive wire inset therein, as opposed to milling large (e.g., several feet in diameter) metal structures to within precise tolerances. Such a device may be less expensive and easier to operate as well as it would likely have less inertia and/or momentum related issues to accommodate.

FIG. 6 illustrates another embodiment of an example shell/core configuration. Specifically, FIG. 6 illustrates a core airgap 506 that is not aligned with an airgap 522 of the shells 512, 518. It will be appreciated that because the core airgap 506 is not aligned with the airgap 522 of the shells 512, 518, the magnetic field yielded from currents in the windings 508, 514 generally does not penetrate, or come into contact with, both the shell 512 of the rotor and the shell 518 of the stator. Thus, the fringe field mitigation elements 520 are merely comprised on, within, and/or approximate one of the two shells, 512, 518. That is, the shell 512 of the rotor 502 may comprise fringe field mitigations elements 520 or the shell 518 of the stator 504 may comprise fringe field mitigation elements, but generally both shells 512, 518 do not need to comprise fringe field mitigation elements 520 because the core airgap 506 is not aligned with the airgap 522 of the shells 512, 518. Stated differently, the magnetic field yielded from currents in the windings 508, 512 that escapes through the gap(s) in the core 510, 516 can be negated, or its effects can be mitigated, by fringe field mitigation elements of shells located approximate the core airgap 506. Because, in the illustrated example, the shell 512 of the rotor 502 extends beyond the core airgap 506, merely the shell 512 of the rotor 502 may comprise fringe field mitigation elements 520 (e.g., comprised of an electrically conductive, substantially continuous material). It will be appreciated that the shell 518 of the stator 504 and/or portions of the shell 512 of the rotor 502 that do not carry a current configured to generate a magnetic field that cancels a magnetic field yielded from the windings 508, 514 (e.g., non-fringe field mitigation element(s) of the shells 512, 518) may be comprised of dielectric material and/or an electrical conductive, discontinuous material, for example. Of course, should the configuration be inverted, mirrored, etc., such that shell 512 is "flat" and shell 518 is "U" shaped instead, then merely shell 518 may comprise fringe field mitigation elements 520.

FIG. 7 illustrates yet another embodiment of an example shell/core configuration. Similar to FIG. 6, FIG. 7 illustrates a core airgap 506 that is not aligned with an airgap 522 of the shell 512. Moreover, at least one of the stator 504 and the rotor 502 may not comprise a shell (e.g., or rather shielding material such as a conductive wire). Rather, merely one of the stator 504 and the rotor 502 may comprise a shell 512 or shielding material, and the fringe field mitigation element(s) 520 may be comprised within the shell 512. For example, as illustrated here, the stator 504 merely comprises windings 514 and a core 516 while the rotor comprises windings 508, a core 510, and a shell 512. In another embodiment, the configurations may be reversed, where the stator 504 comprises a shell 518 and the rotor 502 does not comprise a shell 512, for example.

As described with respect to FIG. 6, because the shell 512 of the rotor 502 extends beyond the core airgap 506 merely the shell 512 of the rotor 502 may comprise fringe field mitigation elements 520 (e.g., comprised of an electrically conductive, substantially continuous material). Portions of the shell 512 of the rotor 502 that are non-fringe field mitigation elements (e.g., and do not have to carry an image current), may be comprised of a dielectric material and/or an electrical conductive, discontinuous material, for example.

It will be appreciated that FIGS. 5-7 merely illustrate several example configurations of a shell/core configuration and that other configurations are also contemplated herein. That is, the scope of the disclosure, including the claims, is not intended to be merely limited to the shell/core configurations herein described. Other configurations for a shell in which an induced current can be used to mitigate radiation and/or mitigate the effects of a magnetic field generated by a net current in windings of a transformer that comprises one or more core airgaps are also contemplated. For example, in another embodiment, the shells 512, 518 are merely positioned at the left and right sides of the cores 510, 516, approximate, adjacent to, etc. the core airgap. That is, the shells 512, 518 do not extend above and below the cores 510, 516 where there is no core airgap.

Figure 8:
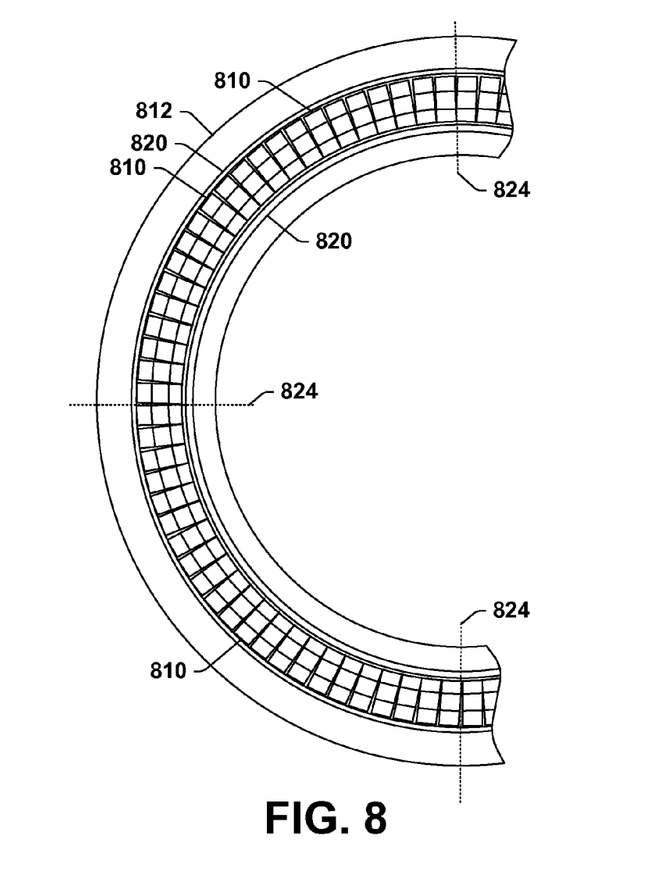
FIG. 8 illustrates a portion of a shell and core segments of a shielded power coupling device.

FIG. 8 is a top-down view of a portion of a shielded power coupling device having a substantially circular configuration and illustrates how such a device may be fabricated in accordance with one or more embodiments provided herein. FIG. 8, for example, illustrates approximately one half of a substantially circular shielded power coupling device, where merely a rotor or stator portion of the shielded power coupling device is illustrated (e.g., a top-down view of FIG. 4 or FIG. 5 merely illustrating the rotor portions 402 or 502). It will be appreciated that, as provided herein, in fabricating such a device a multiplicity of commercially available core 810 (e.g., 410 or 510 in FIG. 4 or 5) segments may be arranged in mutually adjacent fashion so as to collectively approximate a core that is substantially annular and/or semitoroidal, and that a plurality of shell 812 (e.g., 412 or 512 in FIG. 4 or 5) segments may similarly be "pieced" together during fabrication. Note that merely core 810 segments and shell 812 are illustrated in FIG. 8, as windings (e.g., 408 or 508 in FIG. 4 or 5) that would be routed along one or more recesses in the core are omitted for simplicity. To complete assembly of shielded power coupling device, the other side (e.g., the secondary side) may be assembled in similar fashion as the side thereof which is illustrated in FIG. 8, except that this other side would be essentially a mirror image of the side illustrated in FIG. 8 so that when windings are placed in the recesses thereof the open faces of the toroidal cores and windings are made to face each other in mutual opposition (e.g., to create a cross-section profile similar to that illustrated in any one or more of FIGS. 4-7). When a shielded power coupling device having planar configuration as in the present embodiment is assembled in such fashion, the primary core and the secondary core will have substantially identical radii of curvature about a common axis of symmetry, a core airgap (e.g., 406 in FIG. 4) intervening axially between the primary core (e.g., 416 in FIG. 4) and the secondary core (e.g., 410 in FIG. 4) such that the primary core and the secondary core are arranged side-by-side, and the axis of symmetry being substantially collinear with the axis of rotation of the power coupling device.

The shell 812 (e.g., 412 in FIG. 4), generally comprises a fringe field mitigation element(s) 820 (e.g., 520 in FIG. 7) and a non-fringe field mitigation element(s) (e.g., which comprises portions of the shell that are not part of the fringe field mitigation element(s) 820). For example, in one embodiment, the fringe field mitigation element(s) 820 comprises a wire that is configured to (e.g., capable of) carrying an induced current that generates a magnetic field that is sufficient to mitigate and/or substantially cancel a magnetic field that is generated from the current in the windings (e.g., 408, 414 in FIG. 4). It will be appreciated that the wire or other electrically conductive material is of sufficient size, thickness, and/or composition to carry a current that substantially corresponds to (e.g., matches) the negative of the net current in the windings. It will also be appreciated that while the fringe field mitigation element(s) 820 is not shown as directly adjacent to the core segments 810 (e.g., such that small, non-fringe field mitigation elements separate the core segments 810 from the fringe field mitigation elements 820), it will be appreciated that as illustrated in FIGS. 5-7, the fringe field mitigation element(s) 820 may be adjacent the core segments, for example.

The non-fringe field mitigation element(s) may comprise dielectric material and/or electrically conductive material, but is generally not required to carry a current that substantially matches a current in the windings. For example, in one embodiment, the non-fringe field mitigation element(s) of the shell are comprised of a polymer, fiberglass, and/or carbon fiber reinforced composite, for example, that is not electrically conductive and is molded and/or manufactured into a toroidal and/or annular structure. Moreover, in such an embodiment, the non-fringe field mitigation element(s) can comprise a groove or recess into which the fringe field mitigation element(s) of the shell (e.g., the wire) may be inserted (e.g., snapped or laid within). It will be appreciated that making the shell out of plastic and inserting a wire into a recess of the shell may make the structure lightweight (e.g., reducing the weight of the CT machine, for example).

In one embodiment, the shell 812 is comprised of a plurality of segments that are coupled together (e.g., to form a substantially circular shell). For example, as illustrated in FIG. 8, the shell 812 may be broken up into four segments (e.g., the intersection of two segments represented by a dashed line 824), which may be bolted or otherwise fastened together (e.g., glued, adhered, welded, screwed, riveted, snapped, and/or latched, etc.). The respective four (or any other number of) segments may be constructed of a dielectric material and/or of an electrically conductive material (e.g., such as a lightweight metal). However, because the segments are merely fastened together (e.g., and do not form a substantially continuous electric loop), the segments are generally not configured to, or not capable of, sustaining an imaging current. Thus, respective segments may comprise a fringe field mitigation element(s) (e.g., a wire), and during the fastening of the segments, the fringe field mitigation element(s) of adjoining segments may be coupled together (e.g., soldered together) to form a substantially continuous electric loop. Alternatively, once the segments are fastened together, a fringe field mitigation element(s) may be added to the shell 812. For example, once segments of aluminum, plastic, wood, etc. are bolted or otherwise fastened together, a wire(s) configured to carry an induced current may be inserted into a recess of the segments. In this way, as opposed to coupling wires at respective joints between segments, the wire may be coupled in merely one location (e.g., merely two solder joints, one on each side of the core 810 is required). Alternatively, the wire may be a solder-less or joint-less loop having a diameter coincident with that of a recess in the shell 812 such that the wire may be placed in the shell anytime during the fabrication process. Thus, it will be appreciated that the shell 812 (e.g., of the rotor or stator or both) may comprise one or more segments or pieces that are assembled together that may have fringe field mitigation element(s) comprised therein at the time of assembly of the shell and/or some or all of the fringe field mitigation elements can be added to some or all of the shell (e.g., of the rotor or stator or both) at any point(s) during the fabrication process. That is, the shell and corresponding fringe field mitigation elements (e.g., of the rotor or stator or both) can be "pieced" together in any order suitable order.

It will be appreciated that creating the shell from a plurality of segments may be beneficial, especially where the shell is substantially comprised of metal. For example, in one embodiment, such as where shielded power coupling device is configured for use in a computed tomography apparatus, the shell may have a diameter of approximately five feet. It will be appreciated that creating such a toroidal structure by machining a piece of metal generally requires specialized equipment. Thus, creating the structure is expensive and time consuming. However, by dissecting the five foot diameter structure into a plurality of segments and machining respective segments individually, equipment that is more readily available may be used and thus the structure may be less expensive to build. Additional advantages and/or savings may be realized where the shell is fabricated from at least some other materials, such as plastic and/or composite, example.

In one embodiment, the shell 810 comprises a recess(es) in which the core segments 810 can be situated. The core segments 810 are generally comprised of a magnetically permeable material, which may comprise, but is not limited to, ferrite, silicon iron, nickel iron alloy, stainless steel, and cobalt iron alloy, for example. Respective core segments generally comprise one or more recesses (e.g., depending upon the number of windings) in which an electrically conductive winding(s) (e.g., 408, 414 in FIG. 4) can be situated. It this way, respective core segments generally appear to have a "C" shape (e.g., FIG. 4) if merely a single winding is configured to be situated therein and an "E" shape (e.g., FIG. 5) if two winding are configured to be situated therein, for example. Moreover, in one embodiment where the shielded power coupling device is configured to be substantially circular, the core segments 810 may be arranged in a substantially toroidal configuration. It will be appreciated that while FIG. 8 illustrates the core (e.g., 410, 416 in FIG. 4) as being comprised of a plurality of core segments 810, in another embodiment, respective cores may be comprised of a single toroidal structure. That is, the primary core and/or the secondary core may be respectively constructed using a single piece of permeable material that is carved, or otherwise sculpted to form the toroidal structure.

It will be appreciated that if, as described above, the shell 812 is constructed in segments, the core segments 810 may be fastened or otherwise situated in the shell 810 before the shell segments 812 are assembled and/or after the shell segments are assembled. Thus, a first half of the power coupling device may be assembled by creating a shell comprised of a dielectric material and/or an electrically conductive material, inserting a wire therein that is configured to carrying an imaging current, fastening a core or core segments 810 to a recess(es) in the shell, and then fastening a winding to a recess(es) of the core, for example. It will be appreciated that a similar process may be repeated to create a second half (e.g., the stator portion) of the shielded power coupling device.

Any suitable material and assembly method may be used for the windings, cores, and shell(s) (e.g., comprising the shielding material) of the shielded power coupling device. Wire(s), e.g., Litz wire, wound around core(s) might typically serve as winding(s), but any suitable material and manufacturing method, including molding, casting, extrusion, and so forth might also be employed. Although practical examples have been described in which large-diameter ferrite cores were built up from multiplicities of core segments, the present disclosure is not limited thereto, it being possible to employ cast, molded, extruded, or like core elements where available. Furthermore, although ferrite has been mentioned as one specific example of a preferred core material, the present disclosure is not limited thereto, it being possible to use silicon iron, nickel iron alloy, cobalt iron alloy, and/or any other suitable material. Although aluminum and/or a plastic polymer has been mentioned as specific examples of preferred shell materials, the present disclosure is not limited thereto, it being possible to alternatively or additionally employ other metal(s), plastic(s), etc.

Figure 9:
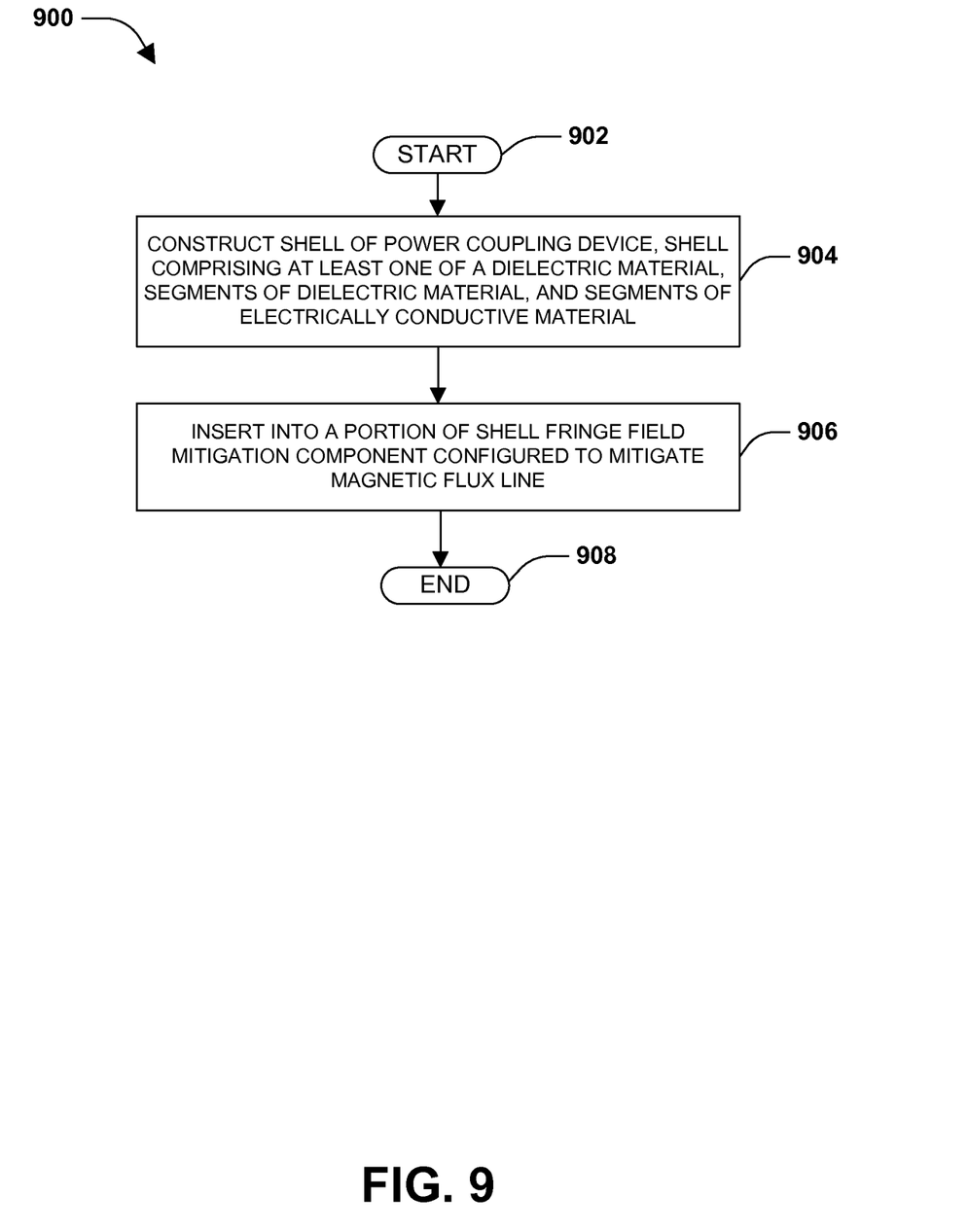
FIG. 9 is a flow diagram illustrating an example method of constructing a shielded power coupling device configured to transfer electric power between a stator and a rotor.

FIG. 9 illustrates one example method 900 of constructing a shielded power coupling device configured to transfer electric power between a stator and a rotor. The method starts at 902 and a shell of the power coupling device is constructed at 904. The shell comprises at least one of a dielectric material (e.g., such as a plastic polymer), segments of dielectric material, and/or segments of electrically conductive material. For example, as illustrated in FIG. 8, respective portions of the shell (e.g., on the rotor side and/or the stator side of the shielded power coupling device), may be divided into segments, and the segments may be constructed individually. For example, in one embodiment, respective segments of the shell are machined according to specified parameters and the segments are bolted or otherwise fastened together (e.g., to form a toroidal structure). In another embodiment, such as where the shell is comprised of a plastic polymer, for example, the shell may be formed by pouring the plastic polymer into a mold and allowing it to harden. Further, sections of plastic and/or other material(s) could be fastened together to form the shell and/or other portions of the shielded power coupling device.

It will be appreciated that the shell is generally comprised of two sections, a stator section and a rotor section (e.g., as described with respect to FIGS. 4-8). Thus, the act of constructing the shell at 904 generally comprises creating two toroidal structures. In one example, the second toroidal structure is substantially a mirror image of the first toroidal structure. However, as discussed above, the shell may be comprised of a greater number of sections or fewer sections. For example, as described with respect to FIG. 7, in one embodiment, merely a rotor portion of the shielded power coupling device may comprise a shell or merely a stator portion of the shielded power coupling device may comprise a shell.

In one embodiment, respective sections (e.g., respective toroidal structures) comprise a recess(es) or a groove(s) for receiving a core, or core segments, of the shielded power coupling device, and the core is arranged within the recess(es). For example, in one embodiment, the core or the core segments are inserted into a recess in the shell that is made to appropriate dimensions for the core and adhered to the shell using an epoxy. In another embodiment, the core or core segments merely rest on top of the shell, for example, and the shell does not comprise a recess(es) for receiving the core.

As described with respect to FIG. 8, an inductive field generating element and an inductive field receiving element are arranged within the core. For example, in one embodiment, a first section of the core is arranged on a rotor portion of the shell and a second section of core is arranged on a stator portion of the shell. The inductive field generating element may be arranged within (e.g., placed on top of) the second section of core and the inductive field receiving element may be arranged within (e.g., placed on top of) the first section of core. For example, a Litz wire or other suitable material may be arranged within the respective sections core (e.g. to form a ring), and may serve as windings in a transformer. It will be appreciated that the number of turns and/or the number of windings may be a function of the desired properties of the shielded power coupling device.

When electric power is applied to the inductive field generating element, an inductive field is generated that may induce a current in the inductive field receiving element (e.g., to generate power in the rotor section of the shielded power coupling device). It will be appreciated that the transfer of electric power from the inductive field generating element to the inductive field receiving element generally generates magnetic fields, or magnetic flux, that are largely shunted by (e.g., confined within) the core, except where magnetic flux escapes therefrom in the vicinity of a core airgap (e.g., an airgap the separates the stator section from the rotor section and allows the rotor section to rotate relative to the stator section of the shielded power coupling device). Such magnetic flux may, in some applications, interfere with sensitive electronics approximate the shielded power coupling device, so, in one embodiment, it is preferable that the magnetic flux is mitigated (e.g., cancelled).

To mitigate or substantially cancel the magnetic flux, at 906 a fringe field mitigation element(s) is inserted into a portion of the shell (e.g. approximate the recess for the core) that is configured to mitigate magnetic flux, and in particular to mitigate magnetic flux that escapes through an airgap in the core. As described above, the fringe field mitigation element(s) is comprised of an electrically conductive material, such as a cooper and/or aluminum wire, for example, and in one embodiment, the electrically conductive material forms a substantially continuous, closed loop, and a current is induced in the electrically conductive material that mitigates or substantially cancels the magnetic flux that escapes through the airgap in the core, for example. It will be appreciated that to mitigate the magnetic flux, the induced current is generally equal in magnitude to a current running through the inductive field generating element and/or the inductive field receiving element but is generally opposite in sign.

It will be appreciated that the fringe field mitigation element(s) (e.g., the wire) can be inserted into portions of the shell before and/or after construction of the shell. For example, in one embodiment, a fringe field mitigation element(s) is inserted into respective segments of the shell before the segments are combined to construct the shell and the fringe field mitigation element(s) of respective, adjacent segments are coupled together (e.g., soldered together), such that, after construction, the fringe field mitigation element(s) forms a closed loop. Those skilled in the art will understand that while the term closed loop is used herein, generally, from an electromagnetic point of view, the loop is continuous and uniform (e.g., and not merely closed). That is the electric and magnetic components of the transformer are generally circularly symmetric (e.g. such that respective sectional views are substantially identical). In another embodiment, the fringe field mitigation element(s) is inserted into the constructed shell. For example, the respective shell segments may be fastened together and then a fringe field mitigation element(s) may be inserted into a recess or groove in the shell, for example, or otherwise attached to the shell. In this way, the fringe field mitigation element(s) may comprise fewer joints (e.g., promoting a more continuous structure). Alternatively, the fringe field mitigation element(s) may be incorporated into one or more portions of the shell (or the entirety of the shell) in any manner(s) and/or at any time(s) during the fabrication process.

It will be appreciated that once the stator section and the rotor section of the shielded power coupling device are constructed, the shielded power coupling device may be coupled to a computed tomography apparatus, and electronics (e.g., such as a radiation source, detector array, etc.) may be coupled to the shielded power coupling device so that power can be supplied to such electronics during operation of the CT apparatus. For example, AC power can be supplied from a stator portion of the CT apparatus to a rotor portion of the CT apparatus via the shielded power coupling device.

At 908 the example method 900 ends.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A shielded power coupling device configured to transfer electric power between a stator and a rotor, comprising:
    an inductive field generating element configured to convert electric power to an inductive coupling field;
    an inductive field receiving element configured to convert the inductive coupling field to electric power;
    a primary and secondary core separated by a core airgap; and
    a shell defined by a plurality of segments, the plurality of segments coupled together to form a substantially circular structure, the shell comprising:
    a fringe field mitigation element comprising an electrically conductive wire that is inserted into the shell once the plurality of segments are coupled together, the fringe field mitigation element configured to mitigate magnetic flux generated by at least one of the inductive field generating element or the inductive field receiving element and escaping from at least one of the primary core or the secondary core near the core airgap, and
    a non-fringe field mitigation element.

2. The device of claim 1, the non-fringe field mitigation element comprising a dielectric material.

3. The device of claim 1, the non-fringe field mitigation element comprising a discontinuous, electrically conductive material.

4. The device of claim 3, the electrically conductive wire being substantially continuous across the plurality of segments.

5. The device of claim 1, the shielded power coupling device configured to transfer electric power operating at a frequency greater than or equal to 20 kHz.

6. The device of claim 1, the shielded power coupling device configured to transfer electric power from a stator portion of a computed tomography device to a rotor portion of the computed tomography device.

7. The device of claim 1, the plurality of segments corresponding to the non-fringe field mitigation element.

8. The device of claim 7, the plurality of segments comprised of a dielectric material.

9. The device of claim 1, the fringe field mitigation element being adjacent the core airgap.

10. A shielded power coupling device for use in a computed tomography apparatus, comprising:
    an inductive field generating element configured to convert electric power to an inductive coupling field;
    an inductive field receiving element configured to convert the inductive coupling field to electric power;
    a primary and secondary core separated by a core airgap; and
    a shell comprising at least two segments that are fastened together to form a substantially toroidal structure, the shell comprising a fringe field mitigation element that is configured to mitigate magnetic flux, escaping from at least one of the primary core or the secondary core near the core airgap, that is generated by at least one of the inductive field generating element or the inductive field receiving element, the fringe field mitigation element comprising an electrically conductive wire that is inserted into the shell once the at least two segments are fastened together.

11. The device of claim 10, the at least two segments comprising a dielectric material.

12. The device of claim 10, the at least two segments defining channels into which the electrically conductive wire is inserted.

13. The device of claim 10, the fringe field mitigation element being adjacent the core airgap.

14. A radiation imaging system, comprising:
    a stator;
    a rotor configured for movement relative to the stator;
    a radiation source coupled to the rotor;
    a detector array coupled to the rotor; and
    a power coupling device configured to transfer electric power between the stator and the rotor for supplying power to at least one of the radiation source or the detector array, comprising:

an inductive field generating element configured to convert electric power to an inductive coupling field;

an inductive field receiving element configured to convert the inductive coupling field to electric power;

a primary and secondary core separated by a core airgap; and a shell comprising:

a fringe field mitigation element comprising an electrically conductive wire and configured to mitigate magnetic flux generated by at least one of the inductive field generating element or the inductive field receiving element and escaping from at least one of the primary core or the secondary core near the core airgap, and a non-fringe field mitigation element comprising at least two segments that are coupled together to form a substantially circular structure, the electrically conductive wire inserted into channels of the at least two segments.

15. The radiation imaging system of claim 14, the at least two segments comprising a dielectric material.

16. The radiation imaging system of claim 14, the fringe field mitigation element and the non-fringe field mitigation element being substantially concentric.

17. The radiation imaging system of claim 14, the fringe field mitigation element being adjacent the core airgap.

18. The radiation imaging system of claim 14, the radiation source comprising an ionizing radiation source.

19. The radiation imaging system of claim 14, the radiation source comprising an x-ray source.

20. The radiation imaging system of claim 14, wherein the radiation imaging system corresponds to a computed tomography (CT) system.

* * * * *